(12) United States Patent
Fletcher et al.

(10) Patent No.: US 9,380,972 B2
(45) Date of Patent: Jul. 5, 2016

(54) BIOLOGICAL FLUID COLLECTION DEVICE AND BIOLOGICAL FLUID COLLECTION AND TESTING SYSTEM

(71) Applicant: Becton, Dickinson and Company, Franklin Lakes, NJ (US)

(72) Inventors: Gary D. Fletcher, Sparta, NJ (US); Ashley Rachel Rothenberg, Morris Plains, NJ (US); Craig A. Gelfand, Jackson, NJ (US); Daniel J. Marchiarullo, Morris Plains, NJ (US); Bradley M. Wilkinson, North Haledon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 89 days.

(21) Appl. No.: 14/251,682

(22) Filed: Apr. 14, 2014

(65) Prior Publication Data
US 2014/0309556 A1 Oct. 16, 2014

Related U.S. Application Data

(60) Provisional application No. 61/811,918, filed on Apr. 15, 2013.

(51) Int. Cl.
*A61B 5/00* (2006.01)
*A61B 5/15* (2006.01)
(Continued)

(52) U.S. Cl.
CPC ......... *A61B 5/150213* (2013.01); *A61B 5/1411* (2013.01); *A61B 5/151* (2013.01);
(Continued)

(58) Field of Classification Search
CPC ........... A61B 5/1411; A61B 5/150305; A61B 5/150343; A61B 5/150755; A61B 5/1405; A61J 1/2096; B01L 3/502753; G01N 1/405; G01N 33/491

USPC .................. 600/576, 573; 604/190, 256, 905, 604/164.11; 210/335, 257.2, 321.62, 210/321.65; 530/390.5, 414, 417, 427; 251/149.1, 149.6; 422/44
See application file for complete search history.

(56) References Cited

U.S. PATENT DOCUMENTS

3,322,114 A 5/1967 Portnoy et al.
3,640,393 A 2/1972 Hurtig
(Continued)

FOREIGN PATENT DOCUMENTS

CN 1382966 A 12/2002
CN 101102847 A 1/2008
(Continued)

OTHER PUBLICATIONS

Membrane Separation Technology for Research and Quality Control, Sartorius AG, Separation Technology, Laboratory Filtration; Mar. 1, 1997.

*Primary Examiner* — Max Hindenburg
(74) *Attorney, Agent, or Firm* — The Webb Law Firm (57) ABSTRACT

A blood collection device adapted to receive a multi-component blood sample is disclosed. After collecting the blood sample, the blood collection device separates a plasma portion from a cellular portion. After separation, the blood collection device is able to transfer the plasma portion of the blood sample to a point-of-care testing device. The blood collection device of the present disclosure also provides a closed collection and transfer system that reduces the exposure of a blood sample and provides fast mixing of a blood sample with a sample stabilizer. The blood collection device is engageable with a blood testing device for closed transfer of a portion of the plasma portion from the blood collection device to the blood testing device. The blood testing device is adapted to receive the plasma portion to analyze the blood sample and obtain test results.

15 Claims, 6 Drawing Sheets

(51) Int. Cl.

| | | |
|---|---|---|
| *G01N 33/49* | (2006.01) | |
| *A61M 1/34* | (2006.01) | |
| *G01N 1/28* | (2006.01) | |
| *G01N 1/40* | (2006.01) | |
| *G01N 1/34* | (2006.01) | |
| *B01L 3/00* | (2006.01) | |
| *B04B 7/08* | (2006.01) | |
| *A61B 5/151* | (2006.01) | |
| *A61B 5/157* | (2006.01) | |

(52) U.S. Cl.
CPC .......... *A61B 5/157* (2013.01); *A61B 5/150022* (2013.01); *A61B 5/15101* (2013.01); *A61B 5/15105* (2013.01); *A61B 5/15144* (2013.01); *A61B 5/15198* (2013.01); *A61B 5/150221* (2013.01); *A61B 5/150267* (2013.01); *A61B 5/150305* (2013.01); *A61B 5/150343* (2013.01); *A61B 5/150351* (2013.01); *A61B 5/150412* (2013.01); *A61B 5/150748* (2013.01); *A61B 5/150755* (2013.01); *A61B 5/150778* (2013.01); *A61M 1/34* (2013.01); *B01L 3/502* (2013.01); *B01L 3/5021* (2013.01); *B04B 7/08* (2013.01); *G01N 1/28* (2013.01); *G01N 1/34* (2013.01); *G01N 1/4005* (2013.01); *G01N 1/4077* (2013.01); *G01N 33/491* (2013.01); *A61B 5/150435* (2013.01); *A61B 5/150442* (2013.01); *A61B 5/150969* (2013.01); *B01L 2200/0631* (2013.01); *B01L 2200/10* (2013.01); *B01L 2300/0681* (2013.01); *B01L 2400/0478* (2013.01); *G01N 2001/4016* (2013.01); *G01N 2001/4088* (2013.01)

(56) References Cited

U.S. PATENT DOCUMENTS

| | | | |
|---|---|---|---|
| 4,511,349 A | 4/1985 | Nielson et al. | |
| 4,627,445 A | 12/1986 | Garcia et al. | |
| 5,055,203 A | 10/1991 | Columbus | |
| 5,163,442 A | 11/1992 | Ono | |
| 5,219,999 A * | 6/1993 | Suzuki | C07K 16/065 530/390.5 |
| 5,422,018 A | 6/1995 | Saunders et al. | |
| 5,636,640 A | 6/1997 | Staehlin | |
| 5,726,026 A | 3/1998 | Wilding et al. | |
| 5,839,715 A * | 11/1998 | Leinsing | A61J 1/2096 251/149.1 |
| 5,922,591 A | 7/1999 | Anderson et al. | |
| 6,074,183 A | 6/2000 | Allen et al. | |
| 6,264,619 B1 | 7/2001 | Ferguson | |
| 6,506,167 B1 | 1/2003 | Ishimito et al. | |
| 6,869,405 B2 | 3/2005 | Marsden | |
| 8,158,410 B2 | 4/2012 | Tang et al. | |
| 2002/0009015 A1 | 1/2002 | Laugharn, Jr. et al. | |
| 2002/0143298 A1 * | 10/2002 | Marsden | G01N 1/405 604/190 |
| 2003/0134416 A1 | 7/2003 | Yamanishi et al. | |
| 2004/0142463 A1 | 7/2004 | Walker et al. | |
| 2004/0143226 A1 | 7/2004 | Marsden | |
| 2004/0230216 A1 | 11/2004 | Levaughn et al. | |
| 2005/0069459 A1 | 3/2005 | Ahn et al. | |
| 2005/0214927 A1 | 9/2005 | Haley | |
| 2006/0029923 A1 | 2/2006 | Togawa et al. | |
| 2006/0240964 A1 | 10/2006 | Lolachi et al. | |
| 2007/0031283 A1 | 2/2007 | Davis et al. | |
| 2007/0160503 A1 | 7/2007 | Sethu et al. | |
| 2008/0135502 A1 | 6/2008 | Pyo et al. | |
| 2008/0240990 A1 | 10/2008 | Flaherty | |
| 2009/0004060 A1 | 1/2009 | Omuro et al. | |
| 2009/0136982 A1 | 5/2009 | Tang et al. | |
| 2009/0181411 A1 | 7/2009 | Battrell et al. | |
| 2009/0204026 A1 | 8/2009 | Crawford et al. | |
| 2010/0089815 A1 * | 4/2010 | Zhang | B01L 3/502753 210/335 |
| 2010/0093551 A1 | 4/2010 | Montagu | |
| 2010/0198108 A1 | 8/2010 | Alden | |
| 2010/0241031 A1 | 9/2010 | Lai | |
| 2011/0124130 A1 | 5/2011 | Wagner et al. | |
| 2011/0124984 A1 | 5/2011 | Rostaing | |
| 2012/0152858 A1 | 6/2012 | Yang | |
| 2012/0275955 A1 * | 11/2012 | Haghgooie | A61B 5/1411 422/44 |
| 2012/0277696 A1 | 11/2012 | Gonzalez-Zugasti et al. | |
| 2012/0277697 A1 | 11/2012 | Haghgooie et al. | |
| 2013/0026085 A1 | 1/2013 | Samsoondar | |
| 2013/0052675 A1 | 2/2013 | Karlsson et al. | |
| 2013/0082012 A1 | 4/2013 | Lean et al. | |
| 2013/0086980 A1 | 4/2013 | Gadini et al. | |
| 2013/0175213 A1 | 7/2013 | Dorrer et al. | |
| 2013/0209331 A1 | 8/2013 | Rodenfels et al. | |

FOREIGN PATENT DOCUMENTS

| | | |
|---|---|---|
| CN | 101332320 A | 12/2008 |
| CN | 102764133 A | 11/2012 |
| DE | 202008010918 U1 | 1/2009 |
| EP | 0376168 A2 | 7/1990 |
| EP | 0747105 A2 | 12/1996 |
| EP | 1096254 A2 | 5/2001 |
| EP | 1106065 A2 | 6/2001 |
| EP | 1477804 A1 | 11/2004 |
| EP | 1602329 A1 | 12/2005 |
| EP | 1627651 A2 | 2/2006 |
| EP | 2264453 A1 | 12/2010 |
| EP | 2413138 A2 | 2/2012 |
| FR | 2929135 A1 | 10/2009 |
| FR | 2977808 A1 | 1/2013 |
| JP | 2004361419 A | 12/2004 |
| WO | 9309710 A1 | 5/1993 |
| WO | 2005018710 A2 | 3/2005 |
| WO | 2006047831 A1 | 5/2006 |
| WO | 2007002579 A1 | 1/2007 |
| WO | 2009123592 A1 | 10/2009 |
| WO | 2011040874 A1 | 4/2011 |
| WO | 2012121686 A1 | 9/2012 |

* cited by examiner

BIOLOGICAL FLUID COLLECTION DEVICE AND BIOLOGICAL FLUID COLLECTION AND TESTING SYSTEM

CROSS-REFERENCE TO RELATED APPLICATION

The present application claims priority to U.S. Provisional Application No. 61/811,918, filed Apr. 15, 2013, entitled "Medical Device for Collection of a Biological Sample", the entire disclosure of which is hereby incorporated by reference.

BACKGROUND OF THE INVENTION

1. Field of the Disclosure

The present disclosure relates generally to devices, assemblies, and systems adapted for use with vascular access devices. More particularly, the present disclosure relates to devices, assemblies, and systems adapted for collecting biological samples for use in point-of-care testing.

2. Description of the Related Art

Blood sampling is a common health care procedure involving the withdrawal of at least a drop of blood from a patient. Blood samples are commonly taken from hospitalized, homecare, and emergency room patients either by finger stick, heel stick, or venipuncture. Blood samples may also be taken from patients by venous or arterial lines. Once collected, blood samples may be analyzed to obtain medically useful information including chemical composition, hematology, or coagulation, for example.

Blood tests determine the physiological and biochemical states of the patient, such as disease, mineral content, drug effectiveness, and organ function. Blood tests may be performed in a clinical laboratory or at the point-of-care near the patient. One example of point-of-care blood testing is the routine testing of a patient's blood glucose levels which involves the extraction of blood via a finger stick and the mechanical collection of blood into a diagnostic cartridge. Thereafter, the diagnostic cartridge analyzes the blood sample and provides the clinician a reading of the patient's blood glucose level. Other devices are available which analyze blood gas electrolyte levels, lithium levels, and ionized calcium levels. Some other point-of-care devices identify markers for acute coronary syndrome (ACS) and deep vein thrombosis/pulmonary embolism (DVT/PE).

Despite the rapid advancement in point-of-care testing and diagnostics, blood sampling techniques have remained relatively unchanged. Blood samples are frequently drawn using hypodermic needles or vacuum tubes attached to a proximal end of a needle or a catheter assembly. In some instances, clinicians collect blood from a catheter assembly using a needle and syringe that is inserted into the catheter to withdraw blood from a patient through the inserted catheter. These procedures utilize needles and vacuum tubes as intermediate devices from which the collected blood sample is typically withdrawn prior to testing. These processes are thus device intensive, utilizing multiple devices in the process of obtaining, preparing, and testing blood samples. Each additional device increases the time and cost of the testing process.

Point-of-care testing devices allow for a blood sample to be tested without needing to send the blood sample to a lab for analysis. Thus, it is desirable to create a device that provides an easy, safe, reproducible, and accurate process with a point-of-care testing system.

SUMMARY OF THE INVENTION

The present disclosure provides a biological fluid collection device, such as a blood collection device, that is adapted to receive a blood sample having a cellular portion and a plasma portion. After collecting the blood sample, the blood collection device is able to separate the plasma portion from the cellular portion. After separation, the blood collection device is able to transfer the plasma portion of the blood sample to a point-of care testing device. The blood collection device of the present disclosure also provides a closed collection and transfer system that reduces the exposure of a blood sample and provides fast mixing of a blood sample with a sample stabilizer. The sample stabilizer can be an anticoagulant, or a substance designed to preserve a specific element within the blood such as, for example, RNA, protein analyte, or other element. The blood collection device is engageable with a blood testing device for closed transfer of a portion of the plasma portion from the blood collection device to the blood testing device. The blood testing device is adapted to receive the plasma portion to analyze the blood sample and obtain test results.

Some of the advantages of the blood collection device and the blood collection and testing system of the present disclosure over prior systems are that it is a closed system which reduces blood sample exposure, it provides passive and fast mixing of the blood sample with a sample stabilizer, and it is capable of transferring pure plasma to a point-of-care testing device. The clinician may collect and separate the blood sample and then immediately transfer the plasma portion to the point-of-care testing device without further manipulation. This enables collection and transfer of plasma to the point-of-care testing device without exposure to blood. Further, for tests which only require small amounts of blood, it eliminates the waste associated with blood collection and plasma separation with an evacuated tube. Also, the blood collection device of the present disclosure incorporates the concepts of lancing, blood collection, and blood separation.

In accordance with an embodiment of the present invention, a biological fluid collection device includes a housing having an inlet port, a transfer port, and a flow channel, with the inlet port and the transfer port in fluid communication via the flow channel. The housing further includes a reservoir adjacent the transfer port and in fluid communication with the flow channel. The device also includes a puncturing element disposed within the housing and adapted for movement between a pre-actuated position wherein the puncturing element is retained within the housing, and a puncturing position wherein the puncturing element extends through the inlet port of the housing and provides fluid communication with the flow channel. The device also includes a separation member disposed within the flow channel between the inlet port and the reservoir, and a wicking element disposed within the flow channel between the inlet port and the separation member.

In certain configurations, the inlet port is adapted to receive a multi-component blood sample. The separation member may be adapted to trap a first component of the multi-component blood sample and allow a second component of the multi-component blood sample to pass therethrough. The separation member may be adapted to trap a cellular component of the multi-component blood sample and allow a plasma component of the multi-component blood sample to pass through the separation member and into the reservoir. In certain configurations, the wicking element may surround at least a portion of the puncturing element. The wicking element may include a sample stabilizer disposed therewith.

The housing may include an actuation mechanism, wherein actuation of the actuation mechanism moves the puncturing element from the pre-actuated position to the puncturing position. The transfer port may include a septum transitionable between a closed position and an open position.

In some configurations, the separation member may be a lateral flow filter or a tangential flow filter. The separation member may include a sample stabilizer disposed therewith.

In accordance with another embodiment of the present invention, a biological fluid collection and testing system includes a biological fluid collection device adapted to receive a multi-component blood sample. The biological fluid collection device includes a housing having an inlet port, a transfer port, and a flow channel, with the inlet port and the transfer port in fluid communication via the flow channel. The housing further defines a reservoir adjacent the transfer port and in fluid communication with the flow channel. The device also includes a puncturing element disposed within the housing and adapted for movement between a pre-actuated position wherein the puncturing element is retained within the housing, and a puncturing position wherein the puncturing element extends through the inlet port of the housing and provides fluid communication with the flow channel. The device further includes a separation member disposed within the flow channel between the inlet port and the reservoir, and a wicking element disposed within the flow channel between the inlet port and the separation member. The system also includes a blood testing device having a receiving port adapted to engage the transfer port of the biological fluid collection device for closed transfer of at least a portion of a component of the multi-component blood sample from the reservoir of the biological fluid collection device to the blood testing device.

In certain configurations, the transfer port includes a septum transitionable between a closed position and an open position. The septum transitions from the closed position to the open position when at least a portion of the transfer port is pressed into the receiving port of the blood testing device. The housing may include an actuation mechanism, wherein actuation of the actuation mechanism moves the puncturing element from the pre-actuated position to the puncturing position. Optionally, the wicking element includes a sample stabilizer disposed therewith. The separation member may be a lateral flow filter or a tangential flow filter. The separation member may include a sample stabilizer disposed therewith. In still further configurations, the blood testing device may be a point-of-care testing device.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

Various point-of-care testing devices are known in the art. Such point-of-care testing devices include test strips, glass slides, diagnostic cartridges, or other testing devices for testing and analysis. Test strips, glass slides, and diagnostic cartridges are point-of-care testing devices that receive a blood sample and test that blood for one or more physiological and biochemical states. There are many point-of-care devices that use cartridge based architecture to analyze very small amounts of blood at a patient's bedside without the need to send the sample to a lab for analysis. This saves time in getting results over the long run but creates a different set of challenges versus the highly routine lab environment. Examples of such testing cartridges include the i-STAT® testing cartridge from the Abbot group of companies. Testing cartridges such as the i-STAT® cartridges may be used to test for a variety of conditions including the presence of chemicals and electrolytes, hematology, blood gas concentrations, coagulation, or cardiac markers. The results of tests using such cartridges are quickly provided to the clinician.

However, the samples provided to such point-of-care testing cartridges are currently manually collected with an open system and transferred to the point-of-care testing cartridge in a manual manner that often leads to inconsistent results, or failure of the cartridge leading to a repeat of the sample collection and testing process, thereby negating the advantage of the point-of-care testing device. Accordingly, a need exists for a system for collecting and transferring a sample to a point-of-care testing device that provides safer, reproducible, and more accurate results. Accordingly, a point-of-care collecting and transferring system of the present disclosure will be described hereinafter. A system of the present disclosure enhances the reliability of the point-of-care testing device by: 1) incorporating a more closed type of sampling and transfer system; 2) minimizing open exposure of the sample; 3) improving sample quality; 4) improving the overall ease of use; and 5) separating the sample at the point of collection.

FIGS. 1-7 illustrate an exemplary embodiment of the present disclosure. The biological fluid collection device of the present disclosure incorporates the concepts of lancing, blood collection, and blood separation. Referring to FIGS. 1-7, a biological fluid collection device 10, such as a blood collection device, of the present disclosure is adapted to receive a blood sample 12 (FIG. 4) having a cellular portion 14 and a plasma portion 16.

Figure 4:
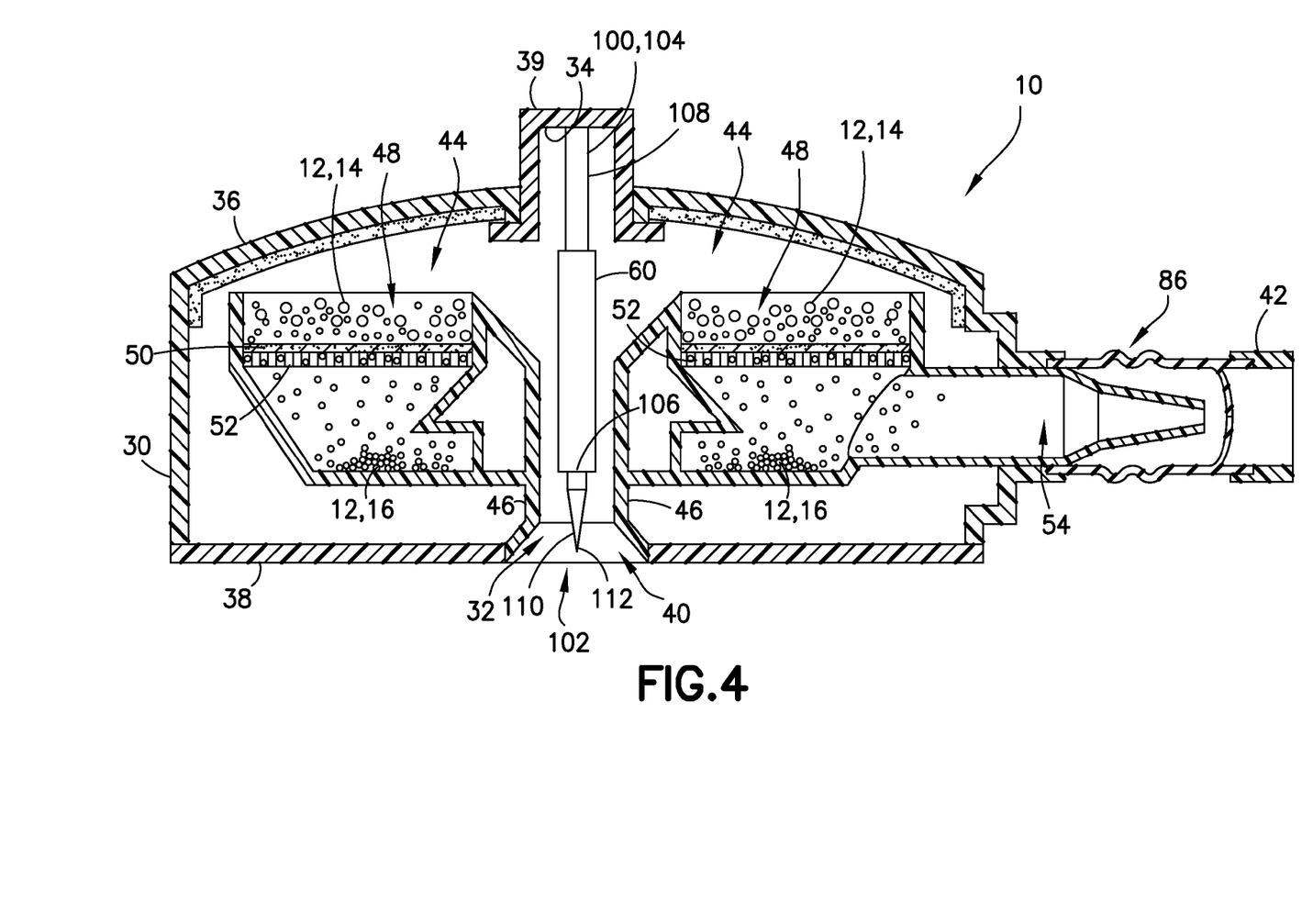
FIG. 4 is a cross-sectional view of the biological fluid collection device of FIG. 2 with a blood sample received within the biological fluid collection device in accordance with an embodiment of the present invention, with a lancet in a pre-actuated position.
Figure 5:
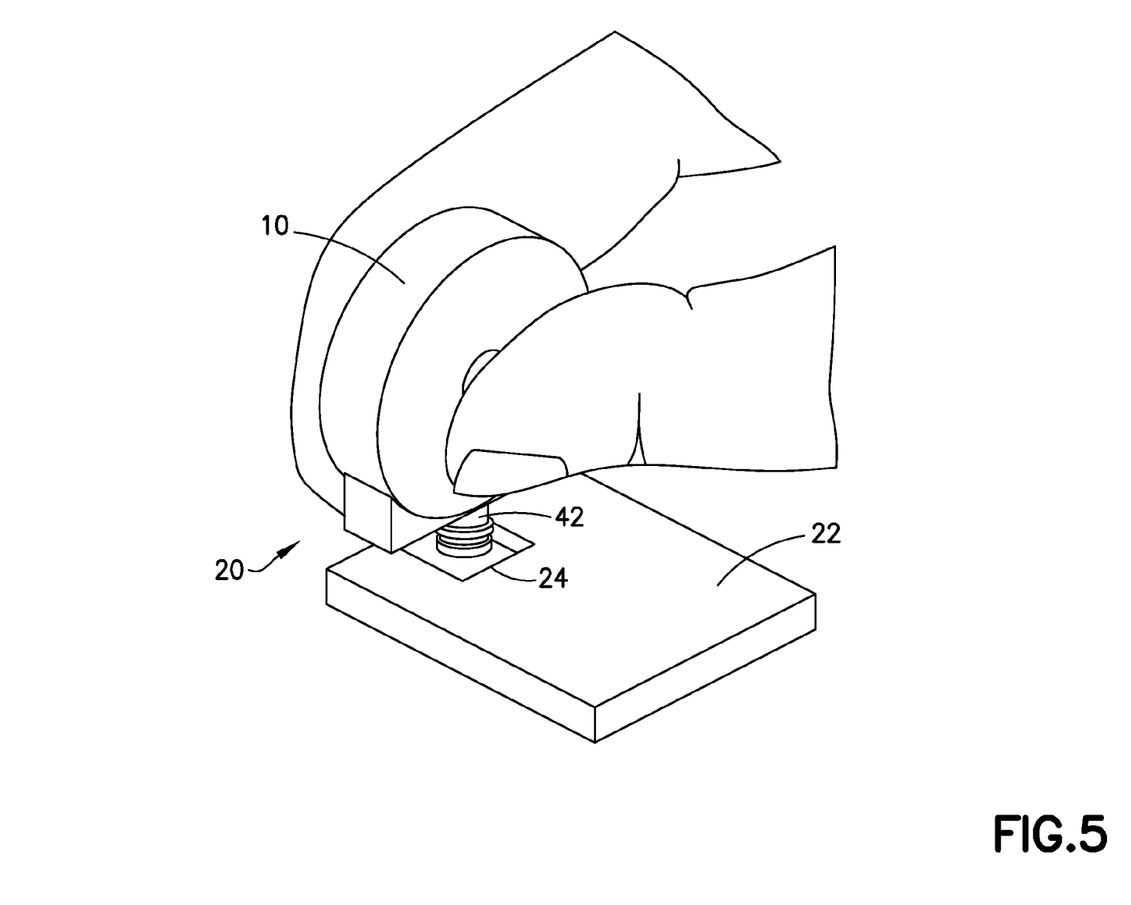
FIG. 5 is a perspective view of a biological fluid collection device and a point-of-care testing device in accordance with an embodiment of the present invention.

FIG. 5 illustrates an exemplary embodiment of the present disclosure. Referring to FIG. 5, a biological fluid collection and testing system 20, such as a blood collection and testing system, of the present disclosure for a blood sample 12 includes a blood collection device 10 adapted to receive a blood sample 12 and a blood testing device or point-of-care testing device 22 engageable with the blood collection device 10 for closed transfer of a portion of the plasma portion 16 (FIG. 4) from the blood collection device 10 to the blood testing device 22. The blood testing device 22 is adapted to receive a portion of the plasma portion 16 of the blood sample 12 to analyze the blood sample and obtain test results.

Some of the advantages of the blood collection device and the blood collection and testing system of the present disclosure over prior systems are that it is a closed system which reduces blood sample exposure, it provides passive and fast mixing of the blood sample with a sample stabilizer, and it is capable of transferring pure plasma to the point-of-care testing device 22. The clinician may collect and separate the blood sample and then immediately transfer the plasma portion to the point-of-care testing device 22 without further manipulation. This enables collection and transfer of plasma to the point-of-care testing device 22 without exposure to blood. Further, for tests which only require small amounts of blood, it eliminates the waste associated with blood collection and plasma separation with an evacuated tube. Also, the blood collection device 10 of the present disclosure incorporates the concepts of lancing, blood collection, and blood separation.

Figure 1:
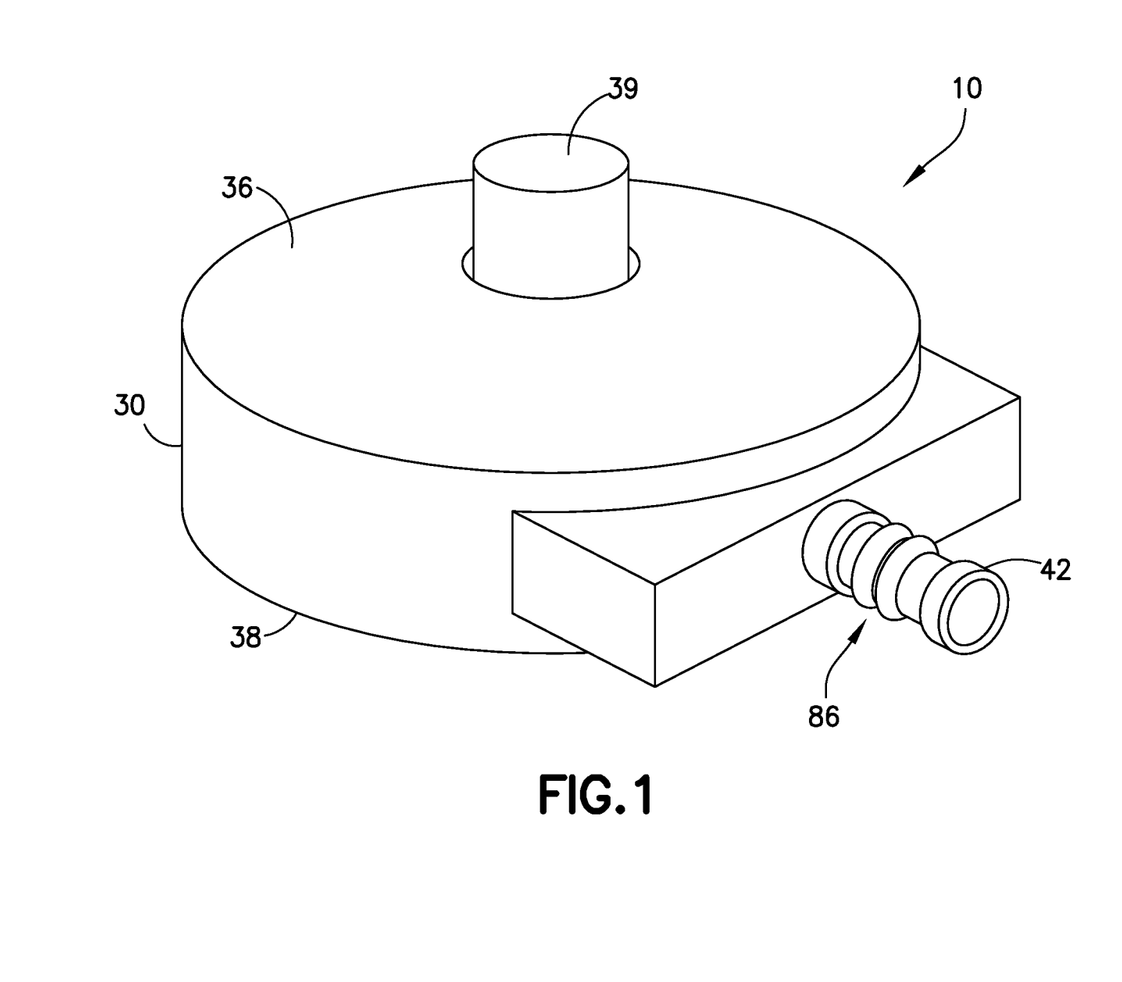
FIG. 1 is a perspective view of a biological fluid collection device in accordance with an embodiment of the present invention.
Figure 2:
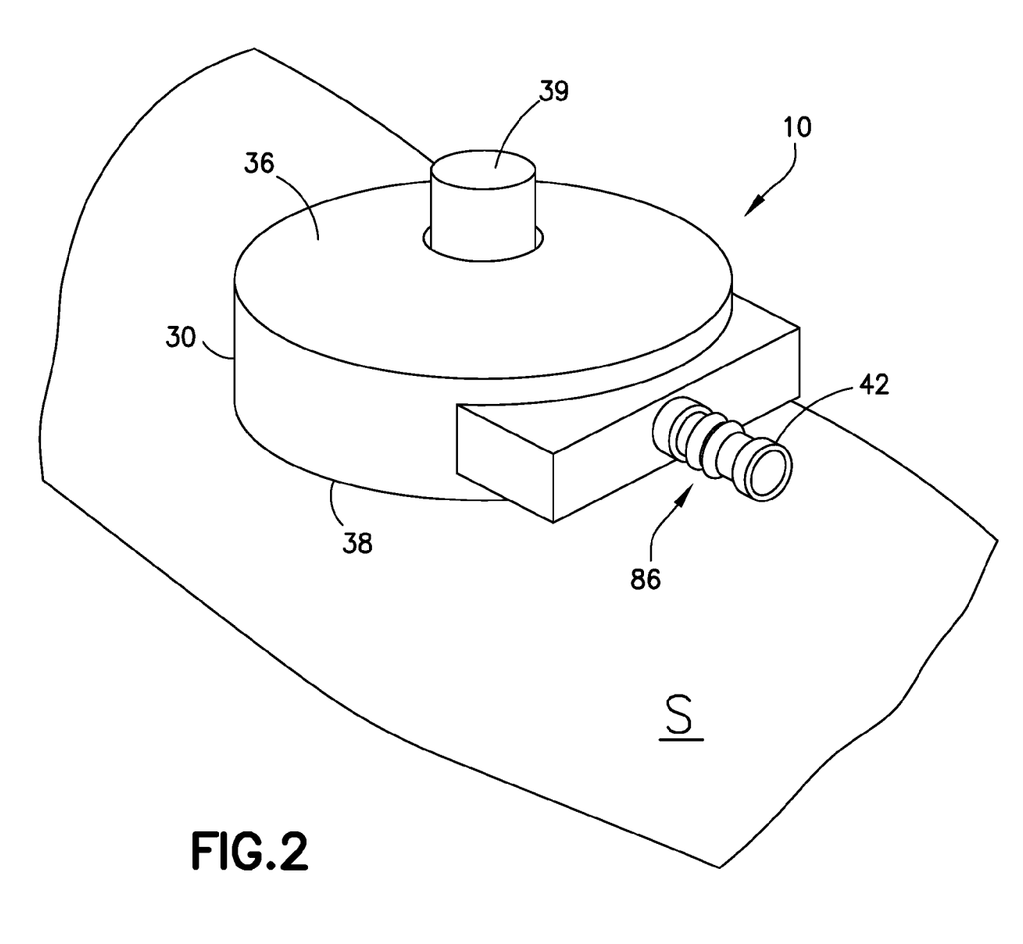
FIG. 2 is a perspective view of a biological fluid collection device secured to a patient in accordance with an embodiment of the present invention.
Figure 3:
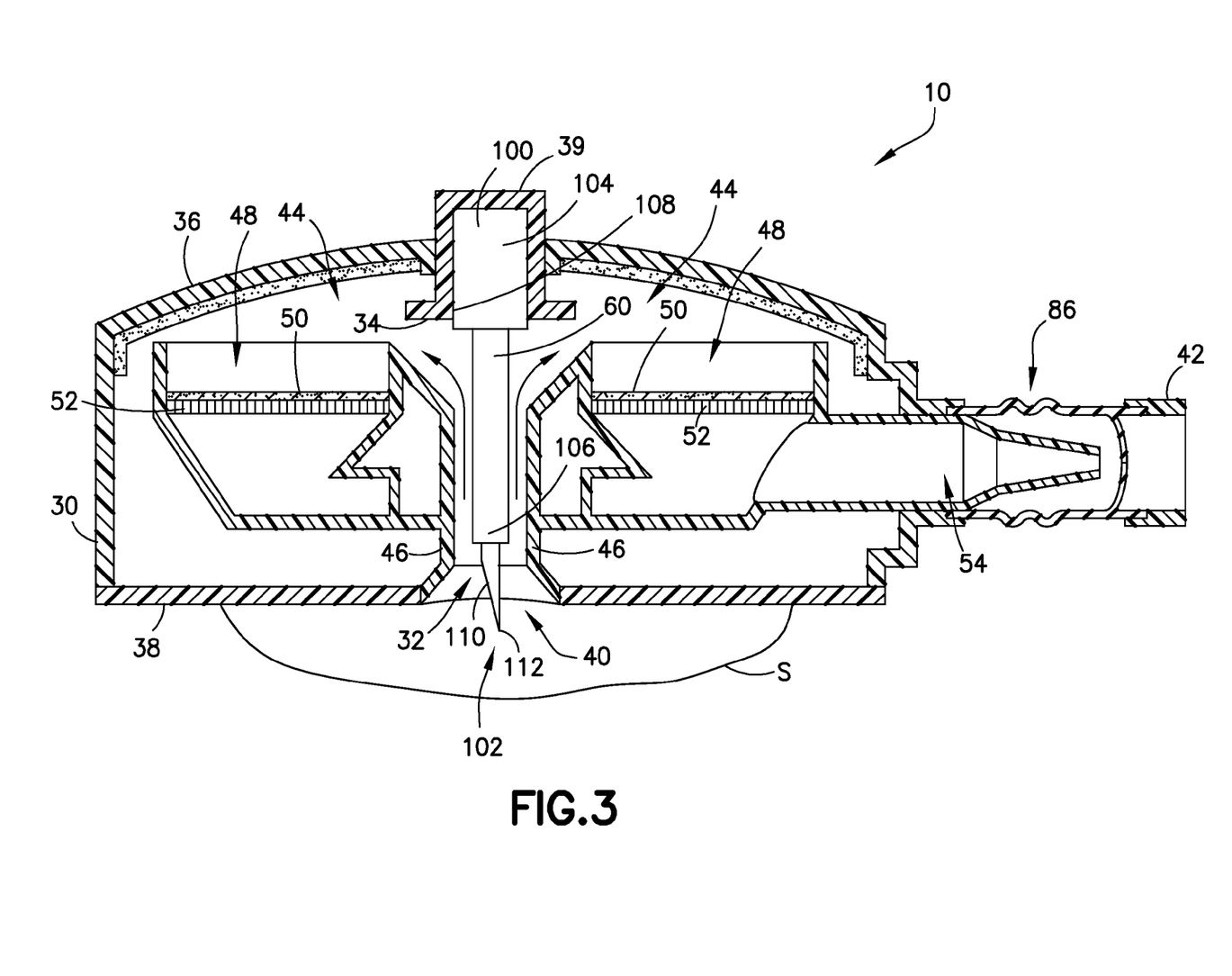
FIG. 3 is a cross-sectional view of the biological fluid collection device of FIG. 2 in accordance with an embodiment of the present invention, with a lancet in a puncturing position.

Referring to FIGS. 1-4, the blood collection device 10 generally includes a housing 30, a central aperture 32, a lancet engagement portion 34, a dome-shaped surface 36, a bottom surface 38, an actuation mechanism or push button 39, an inlet port 40, an outlet port or transfer port 42, a flow channel 44, a wicking element 46, an entry reservoir 48, a sample stabilizer 50, a filter 52, an exit reservoir 54, and a valve or septum 86. The housing 30 defines a central aperture 32 therethrough. A lancet or lancet device 60 is positioned within the central aperture 32 as shown in FIG. 3. The housing 30 includes a lancet engagement portion 34 for securing the lancet 60 within the central aperture 32 as shown in FIG. 3.

The housing 30 includes a dome-shaped surface 36 and a bottom surface 38. Referring to FIG. 2, in one embodiment, the bottom surface 38 includes an adhesive so that the blood collection device 10 can be secured onto a skin surface S of a patient where a blood sample will be accessed. In one embodiment, the adhesive of the bottom surface 38 is protected by a peel-off layer, similar to an adhesive bandage, which would be removed before placing the blood collection device 10 on the skin surface S of the patient's body. A hydrogel or other layer could be included to provide some thickness to the bottom surface 38 and help improve the stability of the adhesive seal. Additionally, in one embodiment, the adhesive could include a chemistry to create a more liquid-tight seal, similar to painter's tape technology, where wetting from the paint itself causes a chemical reaction with the adhesive to create a more water-tight barrier to prevent the paint from seeping under the tape.

Referring to FIG. 3, the housing 30 of the blood collection device 10 generally includes an inlet port 40 defined through the bottom surface 38, an entry reservoir 48 in fluid communication with the inlet port 40 via the flow channel 44, an exit reservoir 54, a filter 52 disposed between the entry reservoir 48 and the exit reservoir 54, an outlet port 42 in fluid communication with the exit reservoir 54, and a valve or septum 86 (FIGS. 6 and 7) disposed in communication with the outlet port 42. In one embodiment, the plasma portion 16 contained within the exit reservoir 54 can be transferred through the valve 86 to the point-of-care testing device 22 as discussed below.

The housing 30 of the blood collection device 10 is adapted to contain a sample stabilizer 50 to provide passive and fast mixing of a blood sample with the sample stabilizer 50. The sample stabilizer 50, can be an anticoagulant, or a substance designed to preserve a specific element within the blood such as, for example, RNA, protein analyte, or other element. In one embodiment, the sample stabilizer 50 is provided within the flow channel 44 adjacent the filter 52. In other embodiments, the sample stabilizer 50 is provided in other areas of the housing 30 of the blood collection device 10 such as the entry reservoir 48.

The housing 30 of the blood collection device 10 includes a separation element, such as a filter 52 disposed between the entry reservoir 48 and the exit reservoir 54 as shown in FIG. 3. The filter 52 is adapted to trap the cellular portion 14 of the blood sample 12 within the entry reservoir 48 and allow the plasma portion 16 of the blood sample 12 to pass through the filter 52 to the exit reservoir 54 as shown in FIG. 4. In one embodiment, the filter 52 includes a tangential flow filter. The tangential flow filter utilizes a cross-flow filtration to separate the plasma portion 16 from the cellular portion 14. Alternatively, the filter 52 may utilize depth filtration.

In one embodiment, the filter 52 may be commercially available hollow fiber membrane filters, or flat membrane filters, such as track-etch filters. Membrane filter pore size and porosity can be chosen to optimize separation of clean (i.e., red blood cell free, white blood cell free, and platelet free) plasma in an efficient manner. In another embodiment, the filter 52 includes a lateral flow membrane. In other embodiments, the filter 52 may comprise any filter that is able to trap the cellular portion 14 of the blood sample 12 within the entry reservoir 48 and allow the plasma portion 16 of the blood sample 12 to pass through the filter 52 to the exit reservoir 54.

The valve 86 is transitionable between a closed position (FIG. 6) to seal a plasma portion 16 of the blood sample 12 within the exit reservoir 54 of the housing 30 and an open position (FIG. 7) to allow a plasma portion 16 to flow through the outlet port 42 to a point-of-care testing device 22 as shown in FIG. 5.

Figure 6:
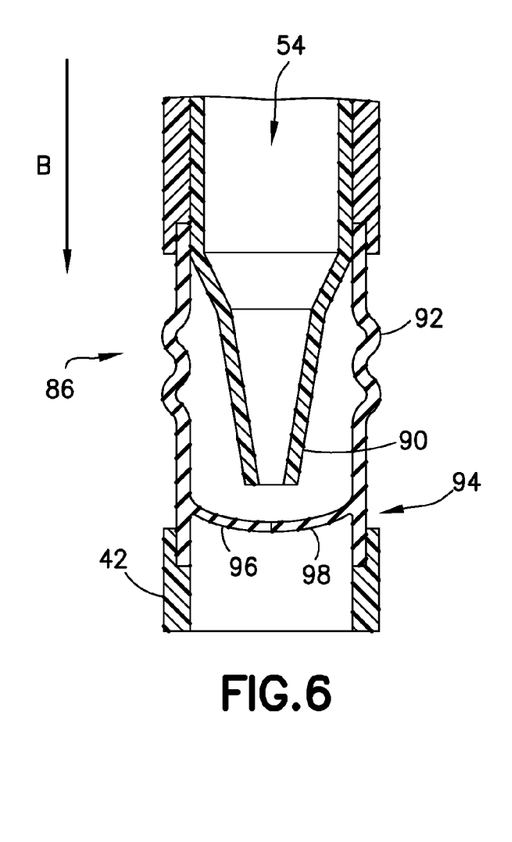
FIG. 6 is a cross-sectional view of a valve of a biological fluid collection device in accordance with an embodiment of the present invention, with the valve in a closed position.
Figure 7:
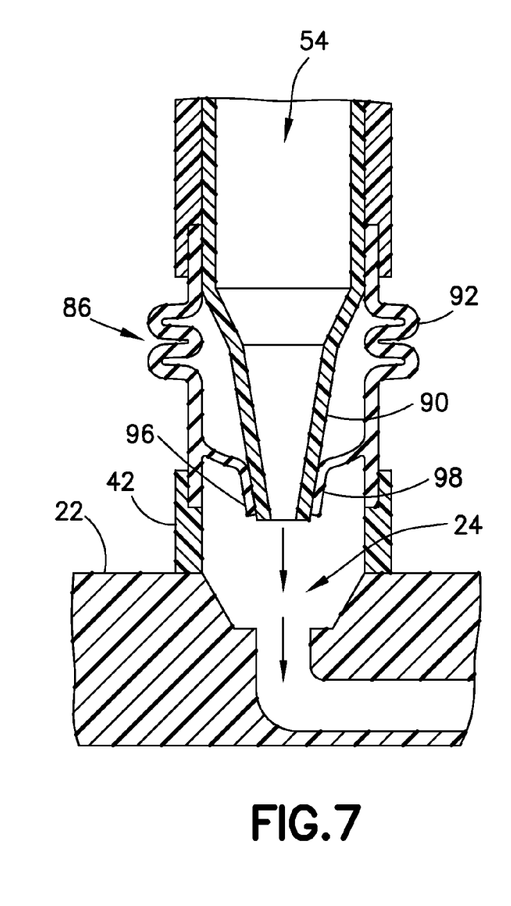
FIG. 7 is a cross-sectional view of a valve of a biological fluid collection device in accordance with an embodiment of the present invention, with the valve in an open position.

Referring to FIGS. 6 and 7, the outlet port 42 of the housing 30 of the blood collection device 10 may include a valve 86 that is transitionable between a closed position and an open position. With the valve 86 in an open position, the plasma portion 16 of the blood sample 12 may flow through the outlet port 42 to a blood testing device or a point-of-care testing device 22 (FIG. 5).

In one embodiment, referring to FIGS. 6 and 7, the valve 86 may generally include a transfer channel 90, a bellows or deformable wall member 92, and a septum or barrier 94 having a first barrier wall 96 and a second barrier wall 98. Referring to FIG. 6, the valve 86 is in a closed position to prevent the plasma portion 16 of the blood sample 12 from flowing through the outlet port 42. In this manner, the plasma portion 16 is sealed within the exit reservoir 54 of the housing 30 of the blood collection device 10. Referring to FIG. 7, the valve 86 is in an open position so that the plasma portion 16 of the blood sample 12 may flow through the outlet port 42 to a blood testing device or a point-of-care testing device 22 (FIG. 5).

Referring to FIG. 6, with the plasma portion 16 received within the exit reservoir 54 of the blood collection device 10, the outlet port 42 of the blood collection device 10 is then positioned over a receiving port 24 of the point-of-care testing device 22. An applied downward force in the direction of arrow B compresses the deformable wall member 92 and opens up the first barrier wall 96 and the second barrier wall 98 of the septum 94 as shown in FIG. 7. With the valve 86 in the open position, the plasma portion 16 of the blood sample 12 is allowed to flow through the receiving port 24 to the point-of-care testing device 22 in a closed manner reducing exposure to the clinician and the patient.

The valve 86 of the blood collection device 10 only opens when the outlet port 42 is pressed upon the receiving port 24 of the point-of-care testing device 22. This releases the isolated plasma portion 16 directly into the receiving port 24 of the point-of-care testing device 22, thus mitigating unnecessary exposure to the patient's blood.

Referring to FIGS. 3 and 4, the blood collection device 10 also includes a lancet or lancet device 60 that may be secured within the central aperture 32 of the housing 30. In one embodiment, the lancet 60 includes a lancet microarray. The lancet 60 generally includes a first end 100, a second end 102, a top portion 104 adjacent the first end 100, a bottom portion 106 adjacent the second end 102, and a housing engagement portion 108. The housing engagement portion 108 engages the lancet engagement portion 34 of the housing 30 for securing the lancet 60 to the housing 30 within central aperture 32 as shown in FIGS. 3 and 4. Referring to FIGS. 3 and 4, a portion of the lancet 60 is disposed within the housing 30 of the blood collection device 10. The bottom portion 106 includes a puncturing element 110 having a puncturing end 112. The puncturing end 112 is adapted for puncturing the skin surface S of a patient (FIG. 2), and may define a pointed end, a blade edge, or a similar cutting mechanism. The puncturing end 112 may include a preferred alignment orientation, such as with a pointed end of a blade aligned in a specific orientation.

The lancet 60 is adapted for movement between a pre-actuated position (FIG. 4) wherein the puncturing element 110 including the puncturing end 112 is retained within the housing 30 and a puncturing position (FIG. 3) wherein the puncturing end 112 of the puncturing element 110 extends through the inlet port 40 of the housing 30 to puncture a skin surface S of a patient to draw a blood sample as discussed in more detail below.

In one embodiment, the housing 30 of the blood collection device 10 may include a self-sealing dock that would allow an external lancet to be removably received within the housing 30. The external lancet could be either pre-integrated into the packaged device or introduced separately by a user before using the blood collection device 10 of the present disclosure.

Referring to FIG. 5, a blood testing device or point-of-care testing device 22 includes a receiving port 24 for receiving the outlet port 42 of the housing 30 of the blood collection device 10. The blood testing device 22 is adapted to receive the outlet port 42 of the housing 30 to analyze the blood sample and obtain test results. The receiving port 24 of the point-of-care testing device 22 allows for the closed transfer of a blood sample from the outlet port 42 of the housing 30 to the point-of-care testing device 22.

Referring to FIGS. 1-7, use of a blood collection device of the present disclosure will now be described. Referring to FIG. 2, upon selecting a site, a clinician can adhere the adhesive on the bottom surface 38 of the housing 30 onto a skin surface S of a patient where a blood sample will be accessed over a selected sampling site.

Referring to FIGS. 2-4, a user or an operator may then actuate or activate the push button 39 of the housing 30 to move the lancet 60 from the pre-actuation position (FIG. 4) to the puncturing position (FIG. 3) thereby causing the lancing of the skin surface S of the patient by the puncturing end 112 of the lancet 60 as shown in FIG. 3. When the push button 39 of the housing 30 is depressed, the puncturing end 112 of the lancet 60 cuts into the skin surface S of the patient's body and capillary blood begins to flow into the inlet port 40 of the housing 30. The wicking element 46 surrounds the inlet port 40, creating a chamber to pool the blood and by a wicking motion collect the blood, pulling it into the blood collection device 10.

In one embodiment, the entry reservoir 48 and/or flow channel 44 of the housing 30 contains a sample stabilizer 50 to promote efficient mixing with the blood sample. The sample stabilizer 50 is added to the blood before it passes through the filter 52 to isolate the plasma. The sample stabilizer 50 is contained either in the wicking element 46, in a coating layer above, within, or on top of the filter 52, or some combination thereof. As such, the blood picks up and mixes with the sample stabilizer 50 as it passes through these portions of the blood collection device 10. Referring to FIG. 3, upon actuation of the lancet 60 to puncture the skin surface S, no or minimal blood will seep between the stick site and the housing 30 of the blood collection device 10, and, importantly, any seeped blood will not subsequently enter the blood collection device 10.

Referring to FIG. 4, the plasma portion 16 of the blood sample 12 may then flow through the filter 52 so that the plasma portion 16 is separated from the cellular portion 14. The plasma portion 16 passes through the filter 52 and into the exit reservoir 54. As the blood passes through the filter 52, platelets, white blood cells, and red blood cells are caught and trapped within the filter 52, allowing only purified plasma to pass through the filter 52 and enter the exit reservoir 54 within the blood collection device 10 for containment until it is dispensed into a point-of-care testing device 22.

Referring to FIG. 5, the next step of the process involves insertion of the outlet port 42 of the blood collection device 10 upon the receiving port 24 of a point-of-care testing device 22. In this manner, the collected plasma portion 16 of the blood sample 12 within the exit reservoir 54 of the blood collection device 10 is transferred to the receiving port 24 of the point-of-care testing device 22 to analyze the collected plasma portion 16 and obtain test results for tests such as glucose, cholesterol, or other blood sample results. The receiving port 24 of the point-of-care testing device 22 allows for the closed transfer of a portion of the plasma portion 16 of the blood sample 12 from the blood collection device 10 to the point-of-care testing device 22. In one embodiment, the plasma portion 16 of the blood sample 12 within the exit reservoir 54 of the blood collection device 10 is dispensed through the valve 86 of the outlet port 42 of the blood collection device 10 into a well or receiving port 24 of the point-of-care testing device 22 to perform the desired test. In one embodiment, the outlet port 42 opens only when the outlet port 42 is pressed upon the receiving port 24 of the point-of-care testing device 22. This releases the isolated plasma directly into the receiving port 24 of the point-of-care testing device 22, thus mitigating unnecessary exposure to the patient's blood.

Some of the advantages of the blood collection device and the blood collection and testing system of the present disclosure over prior systems are that it is a closed system which reduces blood sample exposure, it provides passive and fast mixing of the blood sample with a sample stabilizer, and it is capable of transferring pure plasma to the point-of-care testing device 22. The clinician may collect and separate the blood sample and then immediately transfer the plasma portion to the point-of-care testing device 22 without further manipulation. This enables collection and transfer of plasma to the point-of-care testing device 22 without exposure to blood. Further, for tests which only require small amounts of blood, it eliminates the waste associated with blood collection and plasma separation with an evacuated tube. Also, the blood collection device 10 of the present disclosure incorporates the concepts of lancing, blood collection, and blood separation.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A biological fluid collection device, comprising:
   a housing having an inlet port, a transfer port, and a flow channel, the inlet port and the transfer port in fluid communication via the flow channel, the housing further defining a reservoir adjacent the transfer port and in fluid communication with the flow channel;
   a puncturing element disposed within the housing and adapted for movement between a pre-actuated position wherein the puncturing element is retained within the housing and a puncturing position wherein the puncturing element extends through the inlet port of the housing and provides fluid communication with the flow channel;
   a separation member disposed within the flow channel between the inlet port and the reservoir; and
   a wicking element disposed within the flow channel between the inlet port and the separation member, wherein the wicking element comprises a sample stabilizer disposed therewith.

2. The biological fluid collection device of claim 1, wherein the inlet port is adapted to receive a multi-component blood sample.

3. The biological fluid collection device of claim 2, wherein the separation member is adapted to trap a first component of the multi-component blood sample and allow a second component of the multi-component blood sample to pass therethrough.

4. The biological fluid collection device of claim 2, wherein the separation member is adapted to trap a cellular component of the multi-component blood sample and allow a plasma component of the multi-component blood sample to pass through the filter and into the reservoir.

5. The biological fluid collection device of claim 1, wherein the wicking element surrounds at least a portion of the puncturing element.

6. The biological fluid collection device of claim 1, wherein the housing includes an actuation mechanism in communication with the puncturing element.

7. The biological fluid collection device of claim 1, wherein the transfer port includes a septum transitionable between a closed position and an open position.

8. The biological fluid collection device of claim 1, wherein the separation member is one of a lateral flow filter and a tangential flow filter.

9. The biological fluid collection device of claim 1, wherein the separation member comprises a sample stabilizer disposed therewith.

10. A biological fluid collection and testing system, comprising:
    a biological fluid collection device adapted to receive a multi-component blood sample, the biological fluid collection device comprising:
       a housing having an inlet port, a transfer port, and a flow channel, the inlet port and the transfer port in fluid communication via the flow channel, the housing further defining a reservoir adjacent the transfer port and in fluid communication with the flow channel,
       a puncturing element disposed within the housing and adapted for movement between a pre-actuated position wherein the puncturing element is retained within the housing and a puncturing position wherein the puncturing element extends through the inlet port of the housing and provides fluid communication with the flow channel,
       a separation member disposed within the flow channel between the inlet port and the reservoir, and
       a wicking element disposed within the flow channel between the inlet port and the separation member, wherein the wicking element comprises a sample stabilizer disposed therewith; and
    a blood testing device having a receiving port adapted to engage the transfer port of the biological fluid collection device for closed transfer of at least a portion of a component of the multi-component blood sample from the reservoir of the biological fluid collection device to the blood testing device.

11. The biological fluid collection and testing system of claim 10, wherein the transfer port includes a septum transitionable between a closed position and an open position.

12. The biological fluid collection and testing system of claim 10, wherein the housing includes an actuation mechanism in communication with the puncturing element.

13. The biological fluid collection and testing system of claim 10, wherein the separation member is one of a lateral flow filter and a tangential flow filter.

14. The biological fluid collection and testing system of claim 10, wherein the separation member comprises a sample stabilizer disposed therewith.

15. The biological fluid collection and testing system of claim 10, wherein the blood testing device is a point-of-care testing device.

* * * * *